US012305158B2

(12) United States Patent
Caroff et al.

(10) Patent No.: US 12,305,158 B2
(45) Date of Patent: May 20, 2025

(54) KIT FOR ANALYZING AND MONITORING A PARAMETER, BY MEANS OF A MOBILE SENSOR, OF A CHEMICAL OR BIOCHEMICAL OR BIOLOGICAL REACTION IN A REACTION CHAMBER

(71) Applicant: COMMISSARIAT A L'ENERGIE ATOMIQUE ET AUX ENERGIES ALTERNATIVES, Paris (FR)

(72) Inventors: Tristan Caroff, Grenoble (FR); Sébastien Brulais, Grenoble (FR); Martin Gauroy, Grenoble (FR); Nadège Nief, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 924 days.

(21) Appl. No.: 17/447,224

(22) Filed: Sep. 9, 2021

(65) Prior Publication Data
US 2022/0073860 A1 Mar. 10, 2022

(30) Foreign Application Priority Data
Sep. 10, 2020 (FR) ...................... 20 09160

(51) Int. Cl.
*H02J 50/10* (2016.01)
*C12M 1/36* (2006.01)
(Continued)

(52) U.S. Cl.
CPC ............ *C12M 41/48* (2013.01); *C12M 23/16* (2013.01); *G01N 33/487* (2013.01); *G01N 33/48792* (2013.01); *H02J 50/10* (2016.02)

(58) Field of Classification Search
CPC ...... C12M 41/48; C12M 23/16; C12M 41/00; G01N 33/487; G01N 33/48792; H02J 50/10
See application file for complete search history.

(56) References Cited

U.S. PATENT DOCUMENTS 5,439,125 A * 8/1995 Bloch ................. A61J 9/00
215/11.1
2002/0105856 A1* 8/2002 Terentiev ............. B01F 35/513
366/279

(Continued)

FOREIGN PATENT DOCUMENTS

BR 0417865 A * 10/2006
CN 104028193 A * 9/2014
(Continued)

OTHER PUBLICATIONS

"Measurements on the Fly—Introducing Mobile Micro Sensors for Biotechnological Applications, Sens. Actuators", Lauterbach, et al., Sensors and Actuators A 287 (2019) 29-38; (Year: 2019).*

(Continued)

*Primary Examiner* — Yoshihisa Ishizuka
*Assistant Examiner* — Toni D Sauncy
(74) *Attorney, Agent, or Firm* — Oblon, McClelland, Maier & Neustadt, L.L.P.

(57) ABSTRACT

A kit, for analyzing and monitoring a parameter of a reaction in a reaction chamber, includes: a hollow tube fastened by its ends to the reaction chamber; and a capsule provided with a sensor and guided along the hollow tube via a magnetized magnetic piston disposed in the hollow tube and controlled by a guide device. The hollow tube imposes a predetermined trajectory on the capsule to maintain the capsule at a distance from any mobile member to prevent the capsule from damage. The hollow tube can extend over the entire depth of (Continued)

the reaction medium to allow measurements over the entire depth of the medium.

20 Claims, 12 Drawing Sheets

(51) Int. Cl.
 *C12M 3/06* (2006.01)
 *G01N 33/487* (2006.01)

(56) References Cited

U.S. PATENT DOCUMENTS

| | | | | |
|---|---|---|---|---|
| 2009/0071983 A1* | 3/2009 | Pritchard | ............ | B05B 15/30 |
| | | | | 222/464.2 |
| 2010/0116034 A1* | 5/2010 | Abbott | ............ | G01N 11/14 |
| | | | | 73/54.35 |
| 2019/0132496 A1* | 5/2019 | Jung | ............ | H04N 23/695 |

FOREIGN PATENT DOCUMENTS

| | | | |
|---|---|---|---|
| EP | 2 065 701 A2 | 6/2009 | |
| EP | 3 285 070 B1 | 2/2020 | |
| FR | 3 053 165 A1 | 10/2017 | |
| WO | WO 2012/130334 A1 | 10/2012 | |
| WO | WO 2018/172424 A1 | 9/2018 | |
| WO | WO-2019210067 A1 * | 10/2019 | ............ C12M 23/14 |
| WO | WO-2020081904 A2 * | 4/2020 | ............ C12M 41/34 |

OTHER PUBLICATIONS

Translated Patent Document—WO2012/130334 AI, Luder et al., included as upload as it is modified from document included on IDS. Translation of text and figures from original document relied upon for examination. (Year: 2012).*

French Preliminary Search Report issued May 14, 2021 in French Application 20 09160 filed on Sep. 10, 2020, 2 pages (with English Translation of Categories of Cited Documents).

Lauterbach et al., "Mobile Sensoren für die Biotechnologie—Ortsunabhängige, Miniaturisierte Prozessmessung" Chemie Ingenieur Technik, 91, No. 12, 2019, pp. 1827-1832 (with English Abstract).

O'Mara et al., "Staying alive! Sensors used for monitoring cell health in bioreactors", Talanta 176, Jan. 1, 2018, pp. 130-139.

* cited by examiner

KIT FOR ANALYZING AND MONITORING A PARAMETER, BY MEANS OF A MOBILE SENSOR, OF A CHEMICAL OR BIOCHEMICAL OR BIOLOGICAL REACTION IN A REACTION CHAMBER

TECHNICAL FIELD

The invention relates to the fields of the pharmaceutical industry, cosmetics, the production of biomass, the agri-food industry.

In particular, the invention relates to a kit for analyzing and monitoring at least one parameter of a chemical or biochemical or biological reaction in a reaction chamber. In particular, the monitoring kit is configured to allow the measurement of at least one parameter of a reaction, for example a biological reaction, and more particularly to establish a map in the reaction chamber of said parameter in order to monitor the homogeneity of the reaction.

PRIOR ART

The multiplication or the culture of microorganisms is broadly implemented in the pharmaceutical industry, cosmetology or the agri-food industry for the production of biomass, for the production of a metabolite or the bioconversion of a molecule of interest, but also winemaking and brewing.

This multiplication is advantageously carried out in a bioreactor which allows to exert control over the culture conditions, and more particularly the reaction parameters such as the temperature, the pH, the level of oxygen, the rate of growth of the biomass . . . . A bioreactor, as illustrated in FIG. 1, comprises a reactive chamber 2 in which a stirrer 3 and an aerator 4 intended, respectively, to homogenize and oxygenate the reaction medium are disposed. The bioreactor further comprises a thermal envelope 5 that allows to impose a thermalization on the reaction medium.

The bioreactor 1 is also provided with sensors, for example sensors of temperature, of pH, of dissolved oxygen, in order to ensure a monitoring of the state of the culture, and, if necessary, adjust, preferably in real time, the culture conditions.

According to a first alternative, these sensors 6, 7, as illustrated in FIG. 1, can be mounted in a fixed manner on rods immersed in the reaction medium.

However, this first alternative is not satisfactory.

Indeed, the sensors maintained fixed only probe the reaction medium in their close environment, and remain, consequently, insensitive to any inhomogeneity of said medium. The data collected by these sensors does not, however, allow to carry out an optimal adjustment of the reaction parameters.

Thus, in order to better report on the inhomogeneity of the reaction medium, it is possible, according to a second alternative, to consider a mobile sensor. Such a sensor is in particular housed in a capsule, for example a spherical capsule. Immersed in the reaction medium, the capsule follows the current(s) imposed by the stirrer and is thus exposed to various zones of the reaction medium.

Examples of mobile capsules available today for the monitoring of the state of the culture include that developed by SensOsphere-Fraunhofer and described in the document [1] cited at the end of the description. This capsule comprises in particular a sensor for measuring pH, a sensor for measuring temperature. It is further provided with a chip for geolocation that allows to monitor in real time its movement in the bioreactor, as well as a means for wireless transmission of data.

Thus, in order to establish a statistical profile of the reaction parameters that is as representative as possible of the reaction medium, it can be considered to implement a plurality of these capsules. The latter can thus collect in a collective manner a large quantity of data. However, the transmission of this data, through the reaction medium, to a receiver remains complicated to implement.

Another capsule, developed by the company SmartINST and described in the documents [2] and [3] cited at the end of the description, can also be implemented. This capsule is provided with a plurality of sensors and allows a transmission by radio frequency of the data collected. Nevertheless, this capsule, devoid of geolocation means, does not allow to establish a map of the data collected, and does not therefore provide the possibility to adjust the reaction parameters in an optimal manner.

The document [4], cited at the end of the description, describes another capsule developed by the company FreeSense. The latter, provided with a sensor for measuring pH and a sensor for measuring temperature, is dedicated to monitoring the fermentation in the reaction medium. The capsule, which does not comprise means for transmitting data, bars any optimization of the reaction parameters in real time. Geolocation means, formed by an accelerometer and a pressure sensor integrated into the capsule, allow to locate the latter. These geolocation means require, however, the implementation of complex algorithms, and more particularly Kalman filtering, very demanding in terms of calculation resources. Moreover, these geolocation means must be very regularly calibrated.

Finally, another capsule described in the document [5] cited at the end of the description can also be implemented. This capsule allows the monitoring of the pH, of the temperature and of the aeration. Nevertheless, the latter is devoid of means for transmission in real time of the data collected, and of geolocation means.

In general, the capsules described above, insofar as their movement in the bioreactor is free, can come in contact with the walls of the bioreactor or blades of the stirrer, and consequently risk being damaged.

Moreover, the trajectory of the capsules in the reaction medium remains random, and does not allow to cover the entire extent of the bioreactor.

Thus, one goal of the present invention is to propose a system for monitoring a reaction in a reactive chamber allowing to limit the risks of damage to the cell.

Another goal of the present invention is to propose a system for monitoring a reaction in a reactive chamber allowing a simplified location with regard to the cells known from the prior art.

Another goal of the present invention is to propose a system for monitoring a reaction in a reactive chamber allowing a simple transfer of the data in real time.

Another goal of the present invention is to propose a system for monitoring a reaction in a reactive chamber allowing to probe the entirety of the volume of said chamber.

DISCLOSURE OF THE INVENTION

The goals of the invention are, at least in part, achieved by a kit for analyzing and monitoring at least one parameter of a chemical or biochemical or biological reaction in a reaction chamber, the kit comprising:

a hollow tube that extends according to two ends called, respectively, first end and second end, intended to be fastened onto walls of the reaction chamber;

a probe capsule in a sliding link with the hollow tube, the probe capsule further comprises at least one sensor configured to measure the at least one parameter, and means for transmitting the data capable of being measured by the at least one sensor;

a magnetic piston housed inside the hollow tube, magnetically cooperating with the probe capsule, so that a movement of said magnetic piston imposes a movement onto the probe capsule;

a control means arranged to control the movement of the magnetic piston;

reception means for receiving the data capable of being transmitted by the transmission means.

According to one embodiment, the probe capsule comprises a guide channel through which the hollow tube passes.

According to one embodiment, the control means comprises indexing means allowing the determination of the position of the probe capsule along the hollow tube.

According to one embodiment, the control means comprises pneumatic means arranged to inject according to one and/or the other of the first and the second end a fluid allowing to impose a movement on the magnetized magnetic piston.

According to one embodiment, the pneumatic means comprise a tank provided with a mobile piston, the movement of which controlled by an actuator, in particular a linear actuator, induces the injection of fluid according to one and/or the other of the first end and the second end.

According to one embodiment, the control means comprises one or more cables arranged to guide the magnetic piston along the hollow tube.

According to one embodiment, the magnetic piston comprises a magnet or an electromagnet intended to ensure the magnetic cooperation between the magnetic piston and the probe capsule.

According to one embodiment, the magnetic piston further comprises the reception means so that the transmission of the data capable of being measured by the at least one sensor is transmitted from the capsule to the magnetic piston according to a radio transmission through the hollow tube.

According to one embodiment, the capsule and the magnetic piston each comprise induction means cooperating with each other and arranged to supply said probe with energy.

According to one embodiment, the capsule comprises a battery intended to ensure the provision of energy necessary for the operation of the at least one probe and of the transmission means.

According to one embodiment, the reception means are housed in an external module intended to be disposed outside of the reaction chamber and against the wall of said chamber.

According to one embodiment, said kit comprises means for charging the battery by induction.

According to one embodiment, the charging means comprise a primary coil housed in the external module and a secondary coil housed in the capsule.

According to one embodiment, the hollow tube forms a helicoid, in particular a helicoid with touching turns, and is configured to be stretched and extend in a substantially linear manner between its first end and its second end.

According to one embodiment, the at least one sensor comprises at least one of the elements chosen from: a sensor for measuring pH, a sensor for measuring temperature, a sensor for measuring a quantity of dissolved oxygen, a sensor for measuring a quantity of carbon dioxide.

The invention also relates to a reactor that comprises:
a reaction chamber that comprises an envelope defining an inner volume;
the kit according to the present invention.

According to one embodiment, the hollow tube is disposed in the inner volume of the envelope, and is fastened to the latter by these two ends so that two openings of the hollow tube associated with each of the ends open towards the outside of the envelope. According to one embodiment, the external module of the kit is arranged so that when the capsule is stopped against said envelope at the first end, the transmission of data is carried out through said envelope.

According to one embodiment, the external module is fastened to said reactor at the first end of the hollow tube.

According to one embodiment, the envelope is formed by an inflatable container that when it is inflated stretches the hollow tube of the kit in such a way as to extend the latter in a linear manner between its first end and its second end.

The invention also relates to a method for monitoring a chemical, biochemical or biological reaction implemented in a reactor according to the present invention, and which comprises the following steps:
a) a step of collecting a set of measurements of at least one parameter with the at least one sensor at various positions of the capsule along the hollow tube;
b) a step of adjusting reaction conditions on the basis of the set of the measurements collected in step a).

BRIEF DESCRIPTION OF THE DRAWINGS

Other features and advantages will appear in the following description of a kit for monitoring a parameter of a reaction according to the invention, given as non-limiting examples, in reference to the appended drawings in which:

FIG. 4 shows the kit provided with mechanical guide means according to a first alternative;

FIG. 5 shows the kit provided with pneumatic guide means according to a second alternative;

FIG. 6 illustrates the mode of communication between the transmission means and the reception means, and the mode of powering the capsule and the magnetized piston;

FIG. 7 illustrates the arrangement of an external module intended to ensure the charging of a battery disposed in the cell and the reception of data collected by the sensor(s);

DETAILED DISCLOSURE OF SPECIFIC EMBODIMENTS

The present invention relates to a kit for analyzing and monitoring at least one parameter of a chemical or biochemical or biological reaction in a reaction chamber. The kit comprises in particular a hollow tube intended to be fastened by its ends to the reaction chamber. The kit is also provided with a capsule, provided with one or more sensors, and capable of being guided along the hollow tube. This guiding is for example carried out via a magnetized magnetic piston disposed in the hollow tube and controlled by guide means.

Finally, the kit comprises means for receiving the data capable of being collected by the at least one sensor.

According to the present invention, the hollow tube imposes a predetermined trajectory on the capsule, and thus allows to maintain said capsule at a distance from any mobile member, such as a stirrer. The capsule is thus preserved from any damage. Moreover, the hollow tube can extend over the entire depth of the reaction medium and thus allows measurements, by the sensor(s), over the entire depth of said medium.

More particularly, the implementation of the hollow tube as a guide allows to probe zones of the reaction medium that would not be probed with a free capsule immersed in said medium.

Figure 1:
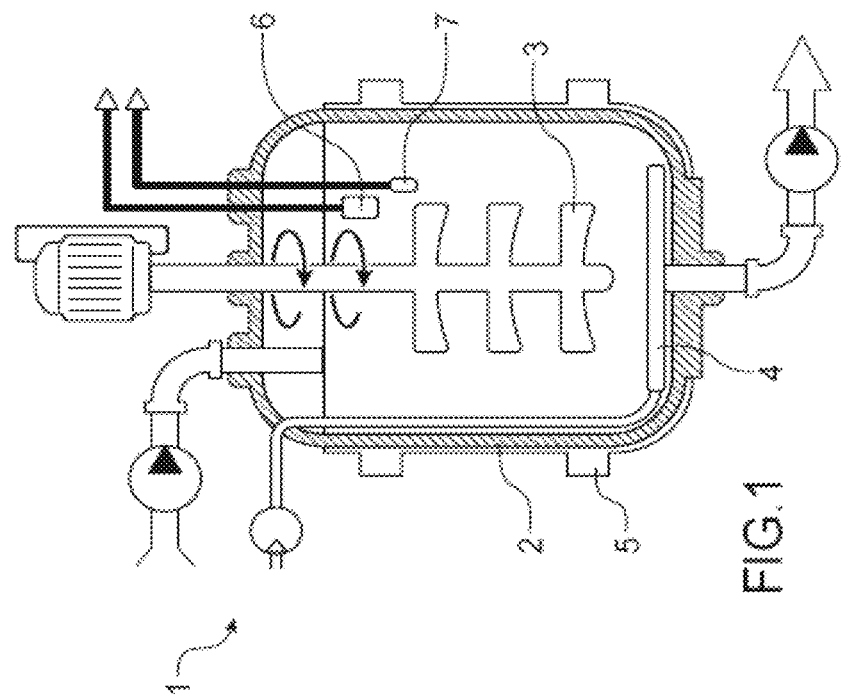
FIG. 1 is a diagram of a reaction chamber, known from the prior art, provided with sensors for monitoring the state of a reaction.
Figure 2:
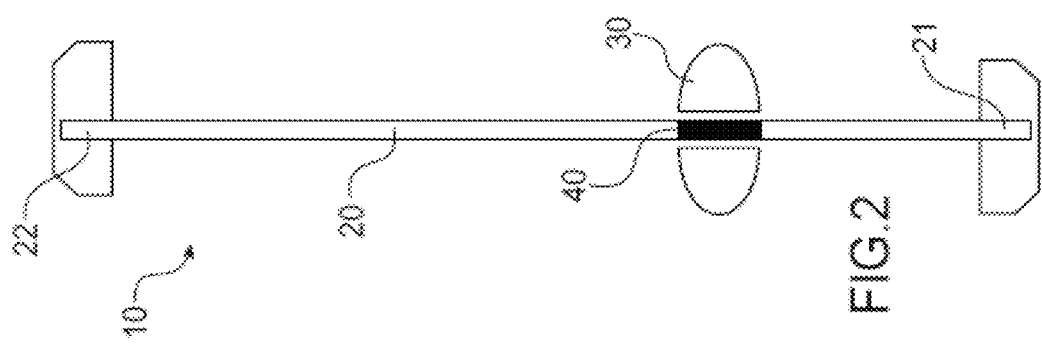
FIG. 2 is a diagram of an analysis and monitoring kit according to the present invention.
Figure 3:
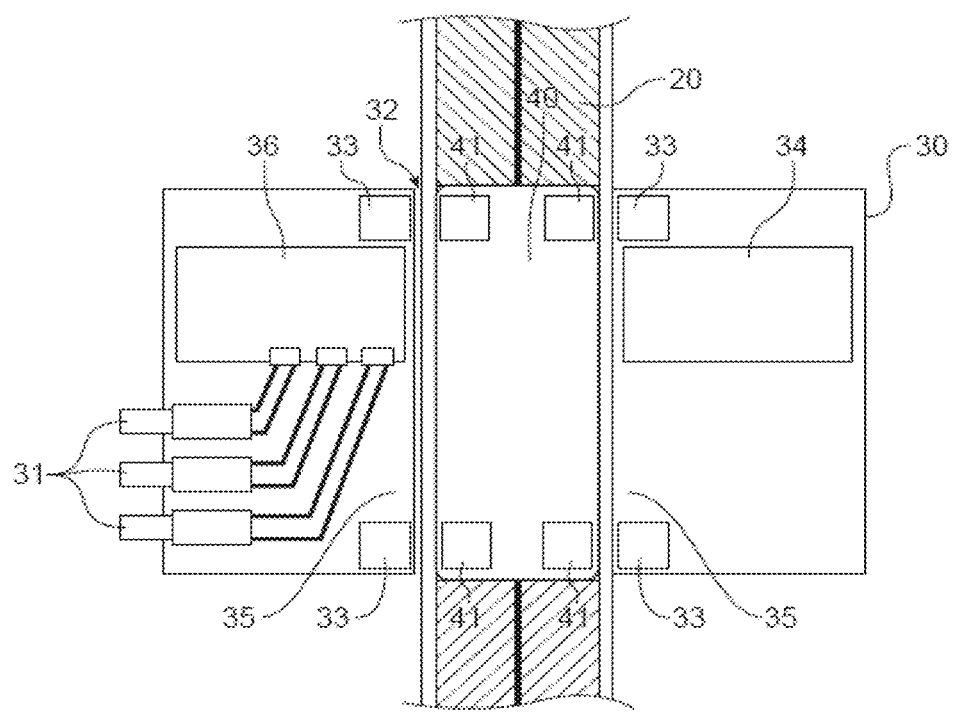
FIG. 3 is a diagram of the arrangement of magnets inside the magnetic piston and the capsule according to the present invention.

The kit 10 according to the present invention is described in relation to FIGS. 2 and 3.

The kit 10 is in particular provided with a hollow tube 20 that comprises two ends called, respectively, first end 21 and second end 22.

The hollow tube 20 can comprise a polymer material and have a diameter of between 1 cm and 5 cm.

The kit 10 also comprises a capsule 30 provided with one or more sensors 31 (FIG. 3), intended to collect data from a reaction medium in which the capsule 30 is capable of being immersed. In this respect, the reaction medium can be a liquid medium in which a chemical, biochemical or biological reaction takes place.

In particular, the data collected by the sensor(s) can be relative to the experimental conditions imposed on the reaction medium. Said conditions can be characteristic of the acidity, of the stirring, of the temperature. The collected data can also be relative to the progress of the reaction or of the phenomena in play in the reaction medium. For example, the sensors 31 can comprise at least one of the elements chosen from: a sensor for measuring pH, a sensor for measuring temperature, a sensor for measuring a quantity of dissolved oxygen, a sensor for measuring a quantity of carbon dioxide. The invention is not limited to only these sensors, and a person skilled in the art, according to the reaction parameters to be monitored, can implement any other sensor.

The capsule 30 according to the present invention is in a sliding link with the hollow tube 20 in such a way as to be able to be guided along said hollow tube 20. The sliding link can, according to an advantageous embodiment, be implemented via a guide channel 32 made in the capsule 30 and through which the hollow tube 20 passes. It is understood that the guide channel passes all the way through the capsule 30.

A magnetic piston 40 (FIGS. 2 and 3) is also housed inside the hollow tube 20. The magnetic piston 40 has a shape, for example cylindrical, complementary to the shape of an inner surface of the hollow tube.

This magnetic piston 40 cooperates magnetically with the capsule 30, so that a movement of said magnetic piston, in the hollow tube, imposes an identical movement on the capsule 30 along said tube. In this respect, the magnetic piston 40 can comprise one or more magnets or electromagnets 41, interacting with other magnets 33 housed in the capsule 30.

The kit 10 also comprises a control means 50 arranged to control the movement of the magnetic piston 40 along the hollow tube 20 and thus drive the capsule 30. This control means, described in detail in the rest of the present invention, can also comprise indexing means allowing the determination of the position of the probe capsule along the hollow tube.

Figure 4:
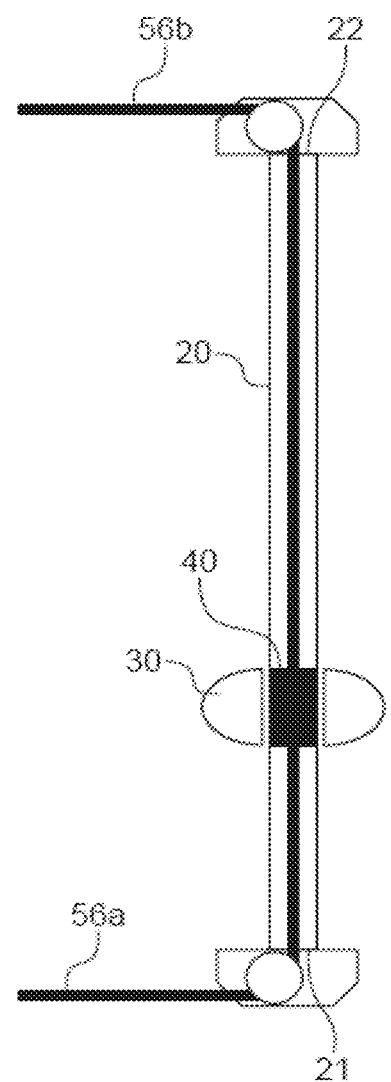
FIG. 4 is a diagram of the kit according to the present invention, in particular

According to a first alternative illustrated in FIG. 4, the control means can comprise mechanical means. In particular, these mechanical means can comprise cables called first cable 56a and second cable 56b, fastened to the magnetic piston 40. In particular, the first cable 56a is arranged to, when it is under tension, attract the magnetized piston 40 towards the first end 21. In an equivalent manner, the second cable 56b is arranged to, when it is under tension, attract the magnetized piston 40 towards the second end 22. More particularly, the first cable 56a is fastened to the magnetized piston 40 and exits the hollow tube at the first end 21. In an equivalent manner, the second cable 56b is fastened to the magnetized piston 40 and exits the hollow tube at the second end 22. The control means according to this first alternative can also comprise a motor, associated with a set of pulleys and/or winches, arranged to exert a tension on one and the other of the first cable 56a and the second cable 56b. According to an alternative to this first variant, a single cable, for example the first cable 56a, can be implemented, by being for example coupled with a floating capsule.

Figure 5:
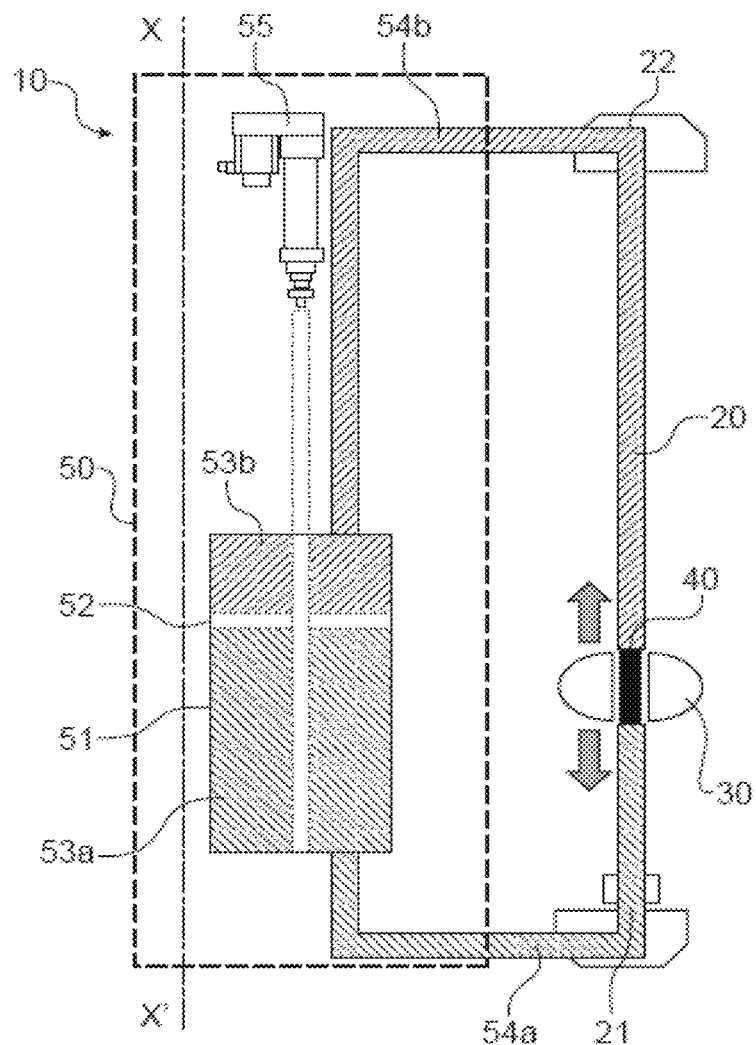
FIG. 5 is a diagram of the kit according to the present invention, in particular

According to a second alternative illustrated in FIG. 5, the control means can comprise pneumatic means. In particular, these pneumatic means are arranged to inject, according to one and/or the other of the first end 21 and the second end 22, a fluid allowing to impose a movement on the magnetic piston 40.

In particular, the pneumatic control means comprises a tank 51 provided with a mobile piston 52 mobile according to an elongation direction XX' of said tank. The mobile piston 52 separates in particular the volume of the tank 51 into two sections having a variable volume called, respectively, first section 53a and second section 53b, and each filled with a fluid, and more particularly an incompressible fluid, for example water. The fluid can also comprise an oil, for example an oil loaded with metal particles allowing to make it electrically conductive.

The first section 53a is fluidly connected to the hollow tube 20 by the first end 21 via a first duct 54a. In an equivalent manner, the second section 53b is fluidly connected to the hollow tube 20 by the second end 22 via a second duct 54b.

Thus, during operation, a movement of the mobile piston 52, leading to a reduction of the volume of the first section 53a, is accompanied by an injection of fluid from the first section 53a towards the first end 21 of the hollow tube 20. During this injection, the magnetic piston 40 is pushed by said fluid in the direction of the second end 22 and drives with it, by magnetic interaction, the capsule 30. The movement of the magnetic piston 40 in the direction of the second end 22 expels the fluid comprised in the hollow tube 20 between said magnetic piston 40 and the second end 22 towards the second section 53b. In an equivalent manner, a movement of the mobile piston 52 leading to a reduction of the volume of the second section 53b is accompanied by an injection of fluid from the second section 53b towards the second end 22 of the hollow tube 20. During this injection, the magnetic piston 40 is pushed by said fluid in the direction of the first end 21 and drives with it, by magnetic interaction, the capsule 30. The movement of the magnetic piston 40 in the direction of the first end 21 expels the fluid comprised in the hollow tube 20 between said magnetic piston 40 and the first end 21 towards the first section 53a.

According to this second alternative, the movement of the mobile piston 52 can be implemented by a drive means, for example a linear actuator 55. The drive means can in this respect comprise the indexing means allowing to determine the position of the capsule on the hollow tube.

The kit 10 according to the present invention also comprises means 34 for transmitting the data capable of being measured by the sensor(s) 31. In particular, the transmission means 34, provided with suitable electronics, can be housed in the capsule 30. Moreover, the transmission means 34 are adapted to cooperate with reception means 60. In particular, the transmission means 34 are adapted to transmit the data collected by the sensor(s) 31 to the reception means 60. This transmission of the data can in particular be caried out according to a wireless communication mode, more particularly radio communication (for example by using the 125 kHz band or the 1356 MHz band).

Figure 6:
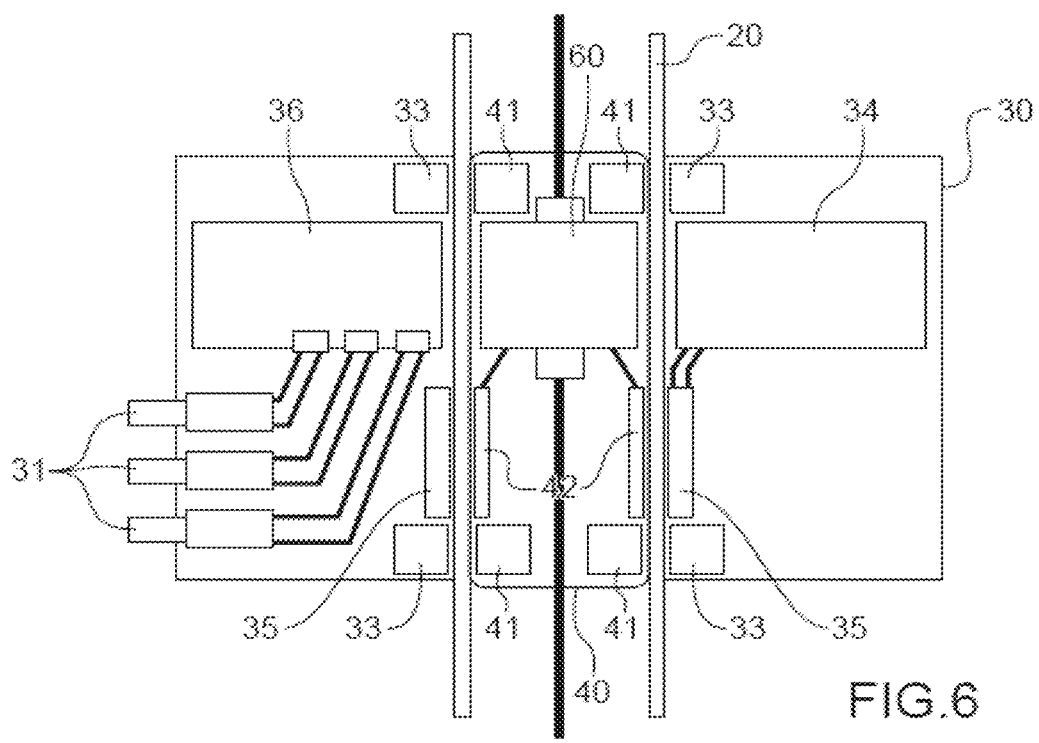
FIG. 6 is a diagram of the capsule and of the magnetic piston according to a first embodiment of the present invention, in particular

According to a first embodiment of the present invention illustrated in FIG. 6, the reception means 60 are housed in the magnetic piston 40. Thus, the wireless communication between the transmission means 34 and the reception means 60 is carried out through the wall of the hollow tube 20. In a particularly advantageous manner, the magnetized piston 40 can be connected to an electric power supply cable intended to power the reception means 60. This electric power supply can also be used for the provision of the energy necessary for the operation of the sensors, of the electronics 36 that are associated with them and of the transmission means. The provision of this energy, from the magnetized piston 40, can implement induction means formed by primary coils 42 and secondary coils 35 respectively carried by the magnetized piston 40 and the capsule 30. The radio communication between the transmission means 34 and the reception means 60 can, in this respect, be ensured by the primary coils 42 and the secondary coils 35.

This arrangement does not require the implementation of a battery or of an accumulator for the operation of the various elements carried by the capsule 30.

Moreover, the radio communication between the transmission means 34 and the reception means 60 through the wall of the hollow tube 20 is only slightly screened or not at all.

The dimensioning of the primary coils and of the secondary coils must allow to satisfy the power needs of such an arrangement according to the first embodiment. In order to better appreciate them, the following example, non-limiting, evaluates the needs and the consumption of the various elements forming the kit according to the present invention. In this respect, the capsule 30 can comprise:
 a pH sensor, the consumption of which is approximately 300 µW;
 one or more temperature sensors, the consumption of which is approximately 20 µW;
 a sensor of dissolved oxygen (DO), the consumption of which is approximately 100 µW;
 electronics associated with the sensors, the consumption of which is approximately 100 µW.

The unit for managing the radio communication is, according to this example, powered by the reception means.

Thus, the needs in terms of total power are approximately 550 µW.

Such a remote powering implementing a Qi (ex BQ51003) protocol, typically capable of delivering a continuous power of 2.5 W, allows to satisfy the energy needs of the kit according to the present invention.

This first embodiment can be advantageously combined with the first alternative. Indeed, the cable(s) implemented in the context of the first alternative can ensure the provision of energy.

Figure 7:
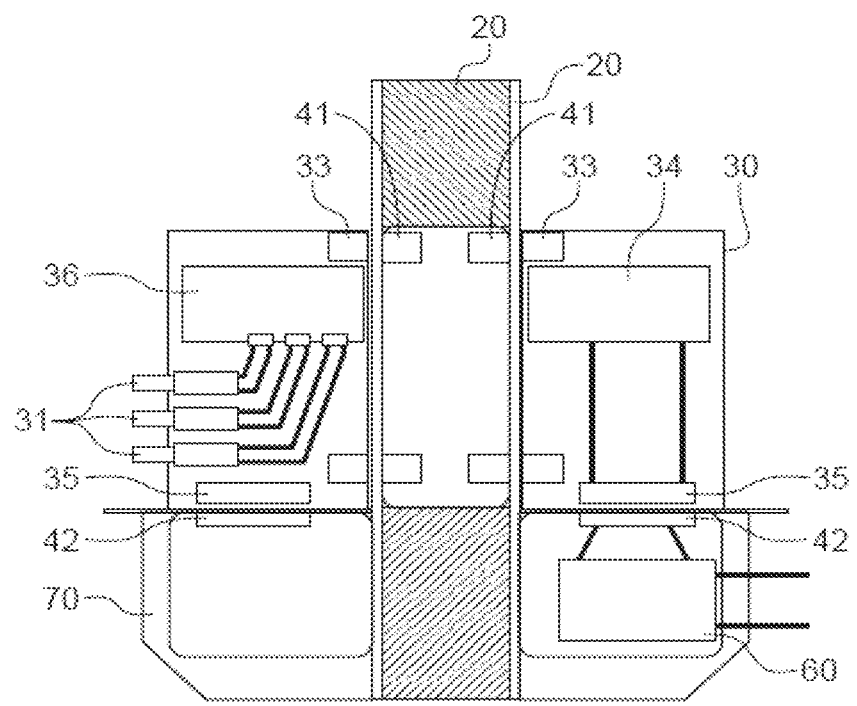
FIG. 7 is a diagram of the capsule and of the magnetic piston according to a second embodiment of the present invention, in particular

FIG. 7 illustrates a second embodiment of the present invention. According to this embodiment, the kit 10 comprises an external module 70 intended to be disposed at the base of the hollow tube, for example at the first end. The external module 70 comprises in particular the reception means 60. In particular, the external module 70 is arranged in such a way as to allow radio communication between the reception means 60 and the transmission means 34 when the capsule 30 is at the end of its trajectory at the first end 21 of the hollow tube 20. Moreover, the capsule 30 can comprise a battery or an accumulator providing the energy necessary for the operation of the sensors, of the electronics 36 that are associated with them and of the transmission means 34. Like in the first embodiment, induction means formed by the primary coils 42 and the secondary coils 35 are also implemented. In particular, the secondary coils 35 are carried by the capsule 30 while the primary coils are carried by the external module 70. Moreover, these primary and secondary coils are arranged to allow the charging or the recharging of the battery housed in the capsule 30 when the capsule 30 is at the end of its trajectory at the first end 21 of the hollow tube 20. The radio communication between the transmission means 34 and the reception means 60 can also be ensured by the primary coils 42 and the secondary coils 35. Thus, the battery or the accumulator allows an autonomous operation of the capsule 30 which can collect data via the sensors 31 that it carries during to and fro movements along the hollow tube. These phases of stopping at the first end, in a "docking" position, can occur in order to transmit the data collected by the sensors to the reception means 60 and recharge the battery. The external module 70 can be disposed outside of the reaction chamber, but in contact with the latter. Thus, the communication between the reception means 60 and the transmission means 34 is carried out through the wall of the reaction chamber.

This second embodiment is advantageously associated with control means according to the second alternative.

The dimensioning of the primary coils and of the secondary coils must allow to satisfy the power needs of such an arrangement according to the second embodiment. In order to better appreciate them, the following example, non-limiting, evaluates the needs and the consumption of the various elements forming the kit according to the present invention. The capsule considered essentially uses the elements described in the context of the dimensioning described above.

According to this second embodiment, it can be considered that the capsule 30 only joins up with the external module at the first end for purposes of transmission of data and recharging of the battery every 300 seconds.

In other words, the battery must be able to store a useful energy $E_{utile}$:

$$E_{utile} = 550 \times 10^{-6} \times 300 = 165 \text{ mJ} \quad \text{[Math 1]}$$

A supercapacitor having a maximum voltage of 5.5V can be considered. Only half of the energy stored in this supercapacitor can effectively be used. Thus, for an electronic arrangement that operates at a voltage of 2.5V, the value C of the capacity of the supercapacitor must satisfy the following relations:

$$E_{cap} = \frac{1}{2}CV^2 \quad \text{[Math 2]}$$

$$C = \frac{2E_{cap}}{V^2} = \frac{2 \times 2 \times E_{utile}}{V^2} = \frac{2 \times 2 \times 165 \times 10^{-3}}{5.5^2} = 21.8 \text{ mF}$$

A supercapacitor having a capacity C equal to 22 mF for example of the Kemet FYH0H223ZF type can advantageously be implemented.

Thus, this supercapacitor, during a recharging phase, which can support a current of approximately 30 mA, is recharged in a time $t_{chg}$:

$$t_{chg} = \frac{C \times dV}{I_{chg}} = \frac{22 \times 10^{-3} \times (5.5 - 2.7)}{0.030} = 2.05 \text{ s} \quad \text{[Math 3]}$$

Moreover, the sensors housed in the probe carry out during the 300 seconds measurements at a frequency of 1 Hz. Thus, the set of data collected follows the following distribution:
- 2 bytes for the pH;
- 6 bytes for 3 temperature sensors;
- 2 bytes for the measurement of dissolved oxygen;
- 4 bytes for the status of the mobile node (battery level and diagnostics);
- 2 bytes for the CRC.

This results in a total of (2+6+2+4)*300=4800 bytes.

It is, in this case, possible to implement a RAM memory having a storage capacity of 20 kB of the type STM32L082.

Moreover, an NFC protocol for transmitting all of the stored data allows to reach a minimum of 106 KB/s (up to 424 KB/s), so that a time of approximately 2 seconds is sufficient for the transmission of the entirety of the data.

Figure 8:
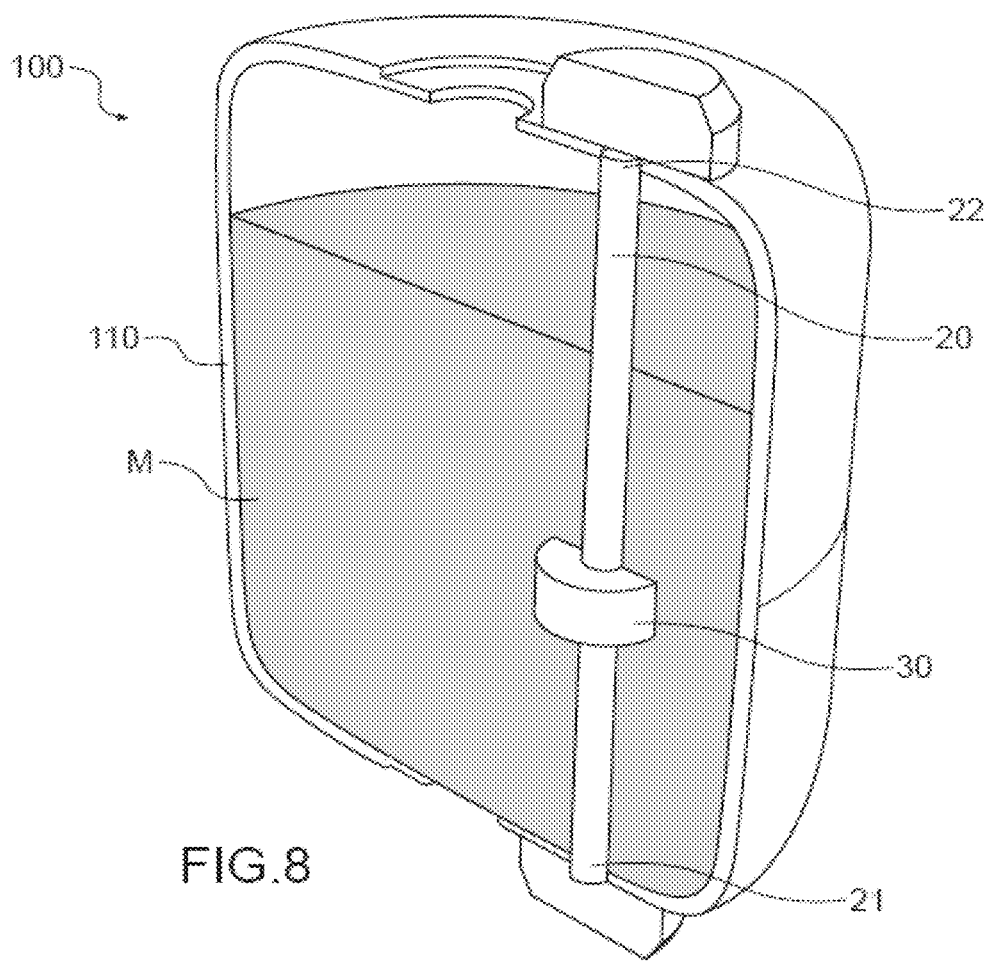
FIG. 8 is a view according to a cutting plane and in perspective of a reactor provided with the kit according to the present invention.

The invention also relates to a reactor 100, for example a bioreactor, provided with a reaction chamber formed by an envelope 110 that defines an inner volume (FIG. 8). The reactor also comprises the kit 10 described above.

During operation, the magnetized piston 40, under the action of the control means 50, can carry out to and fro movements along the tube and thus collect, with its sensors, data characteristic of a state of the reaction medium M filling the inner volume.

The hollow tube 20 fastened to the envelope 110 by these two ends determines the trajectory effectively followed by the capsule 30. Such an arrangement allows to force the capsule 30 to probe zones of the reaction medium that would not be probed if said capsule was not guided. The hollow tube can, according to the needs, extend between its two ends in a linear manner or according to any other shape capable of being adopted by a tube.

Moreover, the hollow tube is arranged so that the openings at its ends open towards the outside of the envelope. These openings thus allow access to the inner volume of the hollow tube 20.

Figure 9:
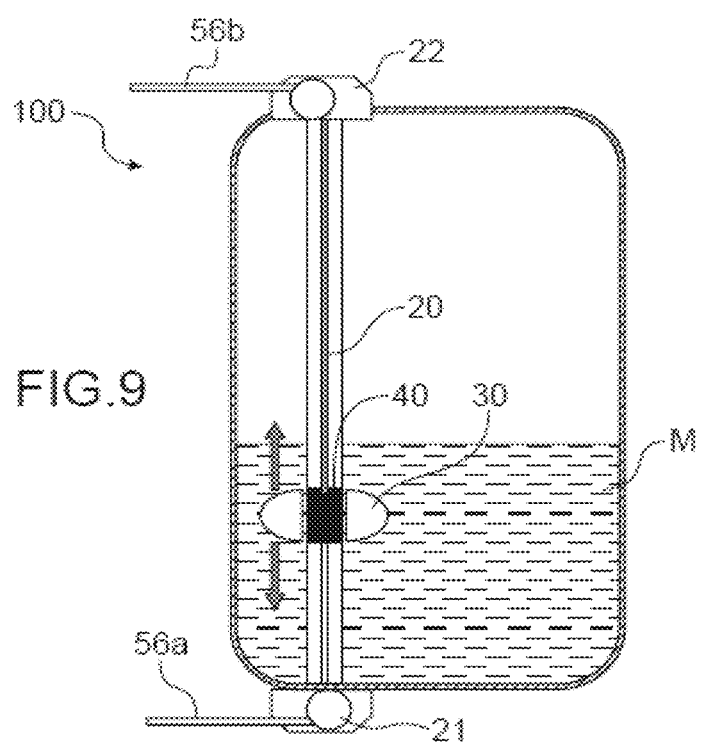
FIG. 9 is a diagram of the reactor implementing the kit provided with control means created according to the first alternative.

FIG. 9 is a diagram of the reactor equipped with the kit 10 provided with the control means according to the first alternative. According to this alternative, the magnetized piston 40 is controlled by a system of cables and drives with it the capsule 30 along the hollow tube 20.

Figure 10:
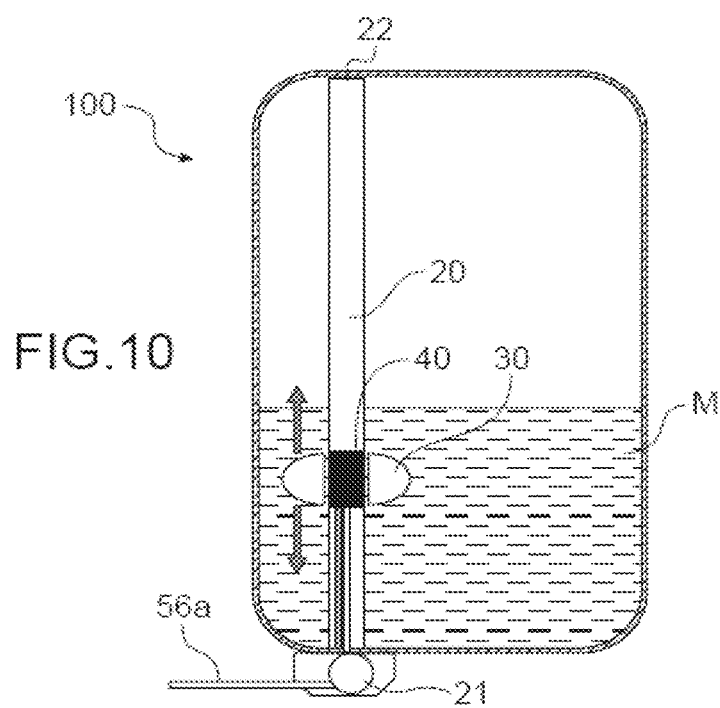
FIG. 10 is a diagram of the reactor implementing the kit provided with control means created according to the first alternative and provided with a single cable coupled with a floating capsule/probe.

According to another aspect illustrated in FIG. 10, the control means can be provided with a single cable, for example only the first cable 56a. Thus, a tension exerted on this first cable 56a allows to direct the capsule 30 towards the first end 21, while a relaxing of this cable 56a allows, by floating of the capsule, to direct the latter towards the second end 22.

Figure 11:
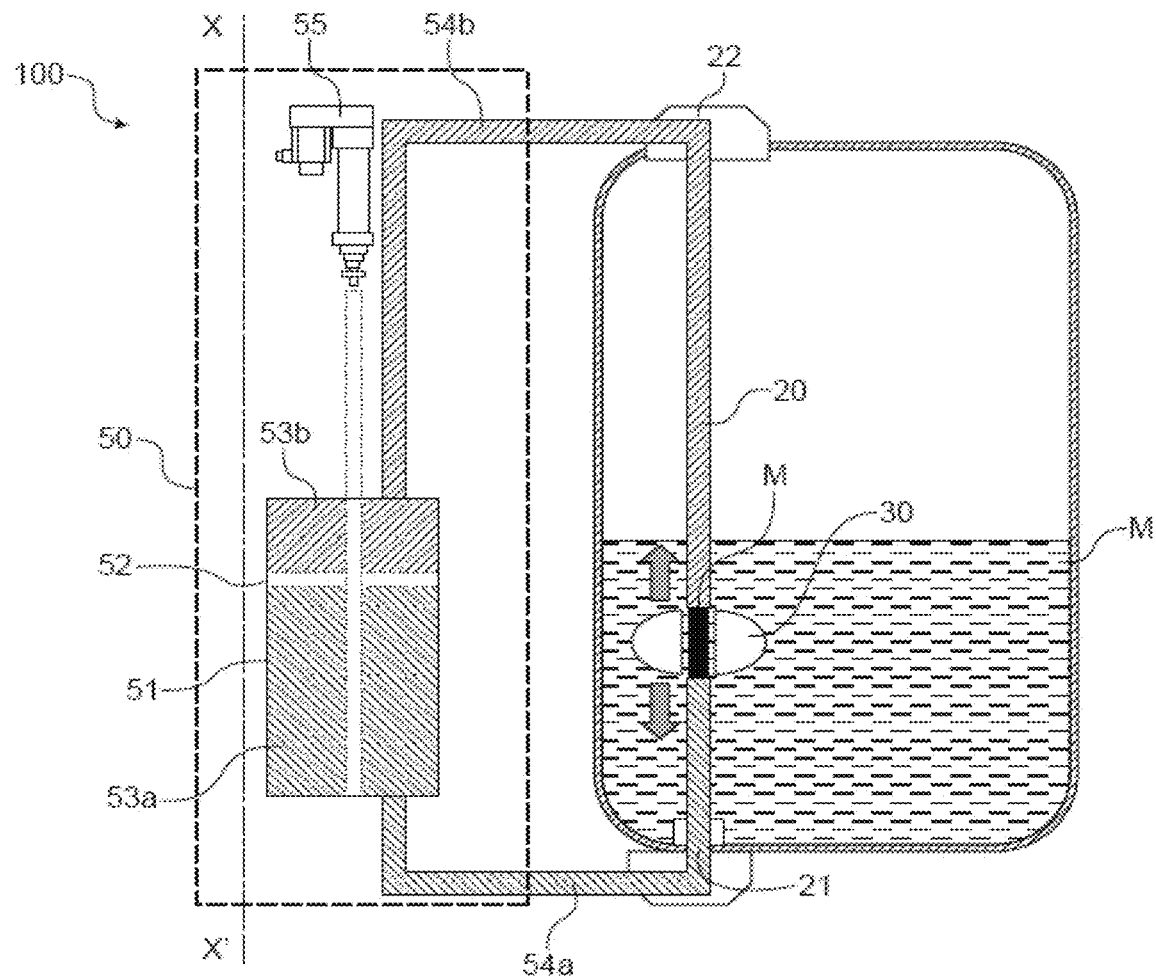
FIG. 11 is a diagram of the reactor implementing the kit provided with control means created according to the second alternative.

Alternatively, and as shown in FIG. 11, the control means of the kit 10, associated with the reactor 100, can be carried out according to the second alternative.

Independently of the alternative relative to the control means, the reception means 60 can be carried out according to a choice of one or the other of the first embodiment and the second embodiment.

In this respect, as soon as the second embodiment is considered, the external module 70, as illustrated in FIG. 7, is fastened to the reaction chamber at the first end 21 of the hollow tube 20. Thus, when the capsule 30 is stopped against the reaction chamber at the first end, radio communication is made possible between the transmission means and the reception means 60. The transmission of data is carried out through said envelope.

Figure 12:
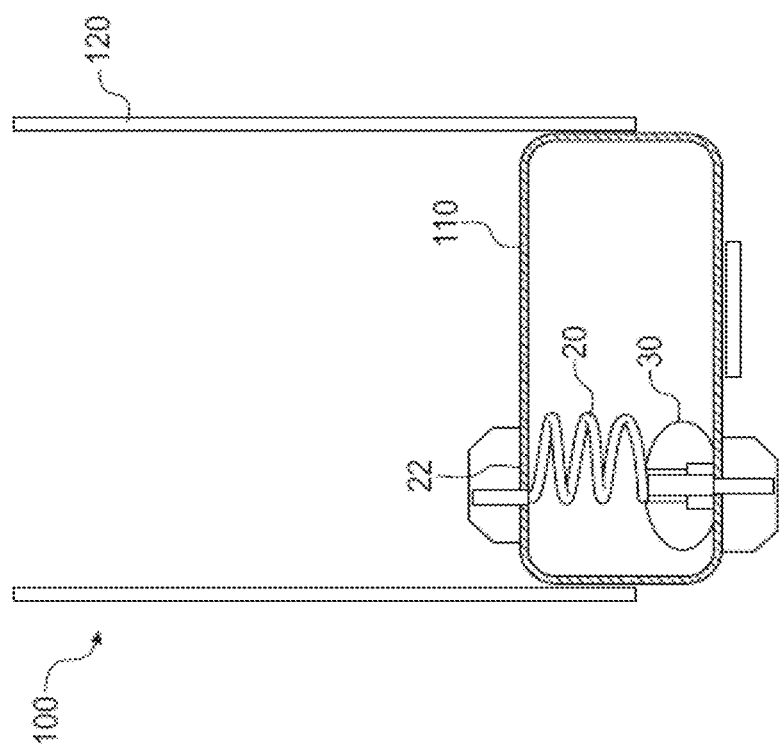
FIG. 12 is a diagram of an inflatable envelope in a deflated state and which comprises a hollow tube in the form of a helicoid.

Advantageously, the external module 70 can cover the hollow tube at the first end 21. According to a particularly advantageous embodiment, the envelope is formed by an inflatable container that when it is inflated can be disposed in a tank 120. This inflatable container can for example be a single-use flexible bioreactor, conventionally used for bioproduction. As for the hollow tube 20, it can be a flexible tube adapted to adopt the shape of a helicoid (for example with touching turns), when no force is applied onto said tube (FIG. 12). In other words, as long as the inflatable envelope is deflated, the hollow tube preserves its shape of a helicoid.

Figure 13:
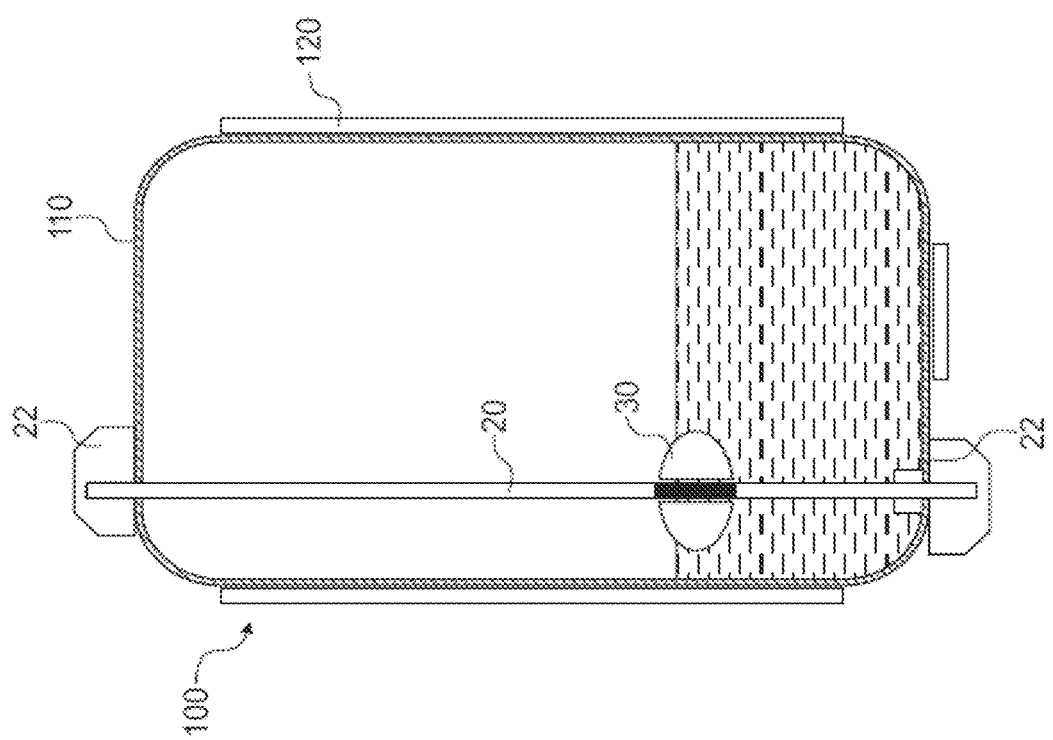
FIG. 13 is a diagram of the envelope of FIG. 12, in an inflated state.

The hollow tube, fastened by its ends to the inflatable envelope, is thus capable of being stretched to form a tube that extends linearly between its first and its second end (FIG. 13). This specific configuration (single-use inflatable container with the hollow tube and measurement cell integrated into the container) allows to guarantee the sterility of the entire system.

The invention also relates to a method for monitoring a chemical, biochemical or biological reaction implemented in a reactor 100 according to the present invention. The method comprises in particular the following steps:
a) a step of collecting a set of measurements of at least one parameter with the at least one sensor at various positions of the capsule along the hollow tube;
b) a step of adjusting reaction conditions on the basis of the set of the measurements collected in step a).

Thus, the implementation of the hollow tube according to the present invention allows to preserve the integrity of the capsule and of the sensors that it carries.

Moreover, the hollow tube that imposes a predetermined trajectory on the capsule opens the door to collecting data in zones not covered by free capsules immersed in the reaction medium.

Moreover, the indexing means associated with the control means allow a simplified location of the capsule in the reaction medium.

Finally, the arrangement proposed limits the screening by the reaction medium of the transfer of the data collected.

REFERENCES

[1] Lauterbach et al., "*Mobile Sensoren fur die Biotechnologie-Ortsunabhangige, miniaturisierte Prozessmessung*", Chem. Ing. Tech., 91, No. 12, 1-7, 2019;
[2] EP3285070;
[3] FR3053165;
[4] WO2018172424;
[5] P.O Mara et al., "*Staying alive! Sensors used for monitoring cell health in bioreactors*", Talanta, Volume 176, Pages 130-139, 1 Jan. 2018.

The invention claimed is:

1. A kit for analyzing and monitoring at least one parameter of a chemical or biochemical or biological reaction in a reaction chamber, the kit comprising:
   a hollow tube that extends according to two ends called, respectively, first end and second end, intended to be fastened onto walls of the reaction chamber;
   a capsule in a sliding link with the hollow tube, authorizing relative translation between the capsule and the hollow tube, the capsule further comprises at least one sensor configured to measure the at least one parameter, and a transmitter for transmitting the data capable of being measured by the at least one sensor;
   a magnetic piston housed inside the hollow tube, magnetically cooperating with the capsule, so that a movement of said magnetic piston imposes a movement onto the capsule;
   a controller arranged to control the movement of the magnetic piston; and
   a receiver for receiving the data capable of being transmitted by the transmitter.

2. The kit according to claim 1, wherein the capsule comprises a guide channel through which the hollow tube passes.

3. The kit according to claim 1, wherein the controller is configured to determine the position of the capsule along the hollow tube.

4. The kit according to claim 1, wherein the controller is arranged to inject in at least one of the first end and the second end a fluid allowing to impose a movement on the magnetized magnetic piston.

5. The kit according to claim 4, wherein the controller comprises a tank provided with a mobile piston, the movement of which controlled by an actuator induces the injection of fluid in at least one of the first end and the second end.

6. The kit according to claim 1, wherein the controller comprises one or more cables arranged to guide the magnetic piston along the hollow tube.

7. The kit according to claim 1, wherein the magnetic piston comprises a magnet or an electromagnet intended to ensure the magnetic cooperation between the magnetic piston and the capsule.

8. The kit according to claim 7, wherein the magnetic piston further comprises the receiver so that the transmission of the data capable of being measured by the at least one sensor is transmitted from the capsule to the magnetic piston according to a radio transmission through the hollow tube.

9. The kit according to claim 7, wherein the capsule and the magnetic piston each comprise inductive portions cooperating with each other and arranged to supply said at least one sensor with energy.

10. The kit according to claim 1, wherein the capsule comprises a battery intended to ensure the provision of energy necessary for operation of the at least one sensor and of the transmitter.

11. The kit according to claim 10, wherein the receiver is housed in an external module intended to be disposed outside of the reaction chamber and against the wall of said chamber.

12. The kit according to claim 11, wherein said kit comprises a charger configured to charge the battery by induction.

13. The kit according to claim 12, wherein the charger comprises a primary coil housed in the external module and a secondary coil housed in the capsule.

14. The kit according to claim 1, wherein the hollow tube forms a helicoid, and is configured to be stretched and extend in a substantially linear manner between the first end and the second end.

15. A reactor comprising:
   a reaction chamber that comprises an envelope defining an inner volume;
   the kit according to claim 1.

16. The reactor according to claim 15, wherein the hollow tube is disposed in the inner volume of the envelope, and is fastened to the inner volume of the envelope by the first and second ends so that two openings of the hollow tube associated with each of the first and second ends open towards the outside of the envelope.

17. The reactor according to claim 15, wherein the external module of the kit is arranged so that when the capsule is stopped against said envelope at the first end, the transmission of data is carried out through said envelope.

18. The reactor according to claim 17, wherein the external module is fastened to said reactor at the first end of the hollow tube.

19. The reactor according to claim 15, wherein the envelope is formed by an inflatable container that when the inflatable container is inflated, the hollow tube of the kit stretches in such a way as to extend the hollow tube in a linear manner between the first end and the second end.

20. A method for monitoring a chemical, biochemical or biological reaction implemented in a reactor according to claim 15, the method comprising:
   a) collecting a set of measurements of at least one parameter with the at least one sensor at various positions of the capsule along the hollow tube; and
   b) adjusting reaction conditions on the basis of the set of the measurements collected in step a).

* * * * *